US00PP08231P

United States Patent [19]

Potter

[11] Patent Number: Plant 8,231

[45] Date of Patent: May 18, 1993

[54] HEBE 'MARGRET'

[75] Inventor: G. Dennis Potter, Pickering, England

[73] Assignee: Blooms of Bressingham, Ltd., Norfolk, England

[21] Appl. No.: 802,003

[22] Filed: Nov. 25, 1991

[51] Int. Cl.[5] ..... A01H 5/00

[52] U.S. Cl. ..... Plt./67.2

[58] Field of Search ..... Plt./67.2

*Primary Examiner*—James R. Feyrer

*Attorney, Agent, or Firm*—Keith D. Gehr

[57] ABSTRACT

A new and distinct cultivar of Hebe having a semi-dwarf to dwarf compact habit. The selection is a profuse bloomer in late May to early June with later flushes in late summer and fall, especially if earlier dead flower spikes have been removed. The flowering racemes stand well above the foliage. Individual blossoms are initially of sky blue color. These fade to a paler blue and then to white, giving an unusual bicolor effect. Because of its compact habit the plant is ideal for use in borders or in containers.

3 Drawing Sheets

The present invention relates to a new and distinct dwarf or semi-dwarf variety of evergreen shrub of the genus Hebe, a member of the Scrofulariaceae or Figwort family.

This new Hebe is the result of a breeding program and is a cross between Hebe 'Carl Teschner' and Hebe 'Mauve Queen'. The new variety has been reproduced from cuttings. Each of the progeny of the first and succeeding generations exhibit characteristics identical to those of the mother plant. The parents were chosen in an attempt to reproduce the hardiness of Hebe 'Carl Teschner' with the profuse flowering ability of Hebe 'Mauve Queen'. This particular selection appears to have accomplished that goal. It has the added characteristic of flowering for a longer period than is usual in the Hebes tending to dwarf habit. These dwarf-tending Hebes most often have small flower spikes in relation to the size of the shrub so that the flowering plant appears to lack continuity. Hebe 'Margret' is a profuse bloomer with relatively large flower spikes. It presents the appearance of an entire shrub being in synchronous heavy bloom rather than showing irregularly distributed blossom spikes.

The habit of Hebe 'Margret' is distinct in that it has the upright characteristics of a taller growing variety with the many flower spikes appearing well above the foliage. This is in contrast to other dwarf Hebes that in many cases have a sprawling habit. The sky blue flower spikes appear in profusion in late May followed by several flushes in late summer and fall, sometimes as late as December. Other Hebes of similar size tend to have an initial flowering period with only spasmodic flowering to follow. As time passes the flowers fade to pale blue and then to white producing an unusual bicolor effect. Continuity of flowering is encouraged by removal of dead flower spikes.

BRIEF DESCRIPTION OF THE PHOTOGRAPHS

DETAILED PLANT DESCRIPTION

Figure 1:
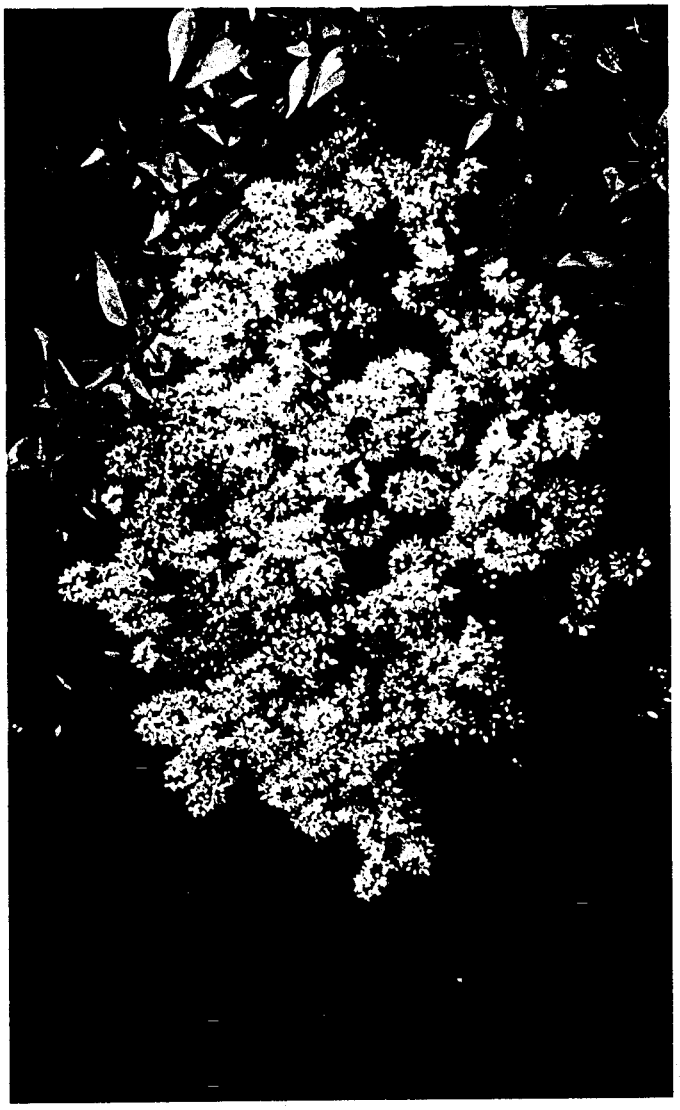
FIG. 1 is a view of Hebe 'Margret' growing in a border setting.
Figure 2:
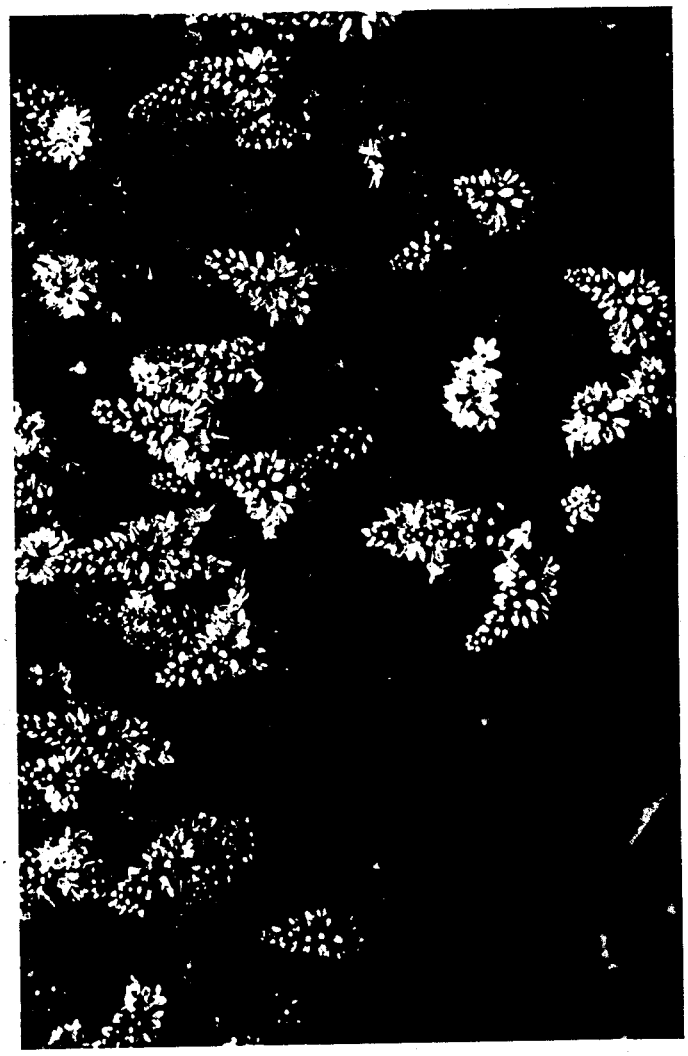
FIG. 2 is a closer view showing bud, flower and leaf color and characteristics.
Figure 3:
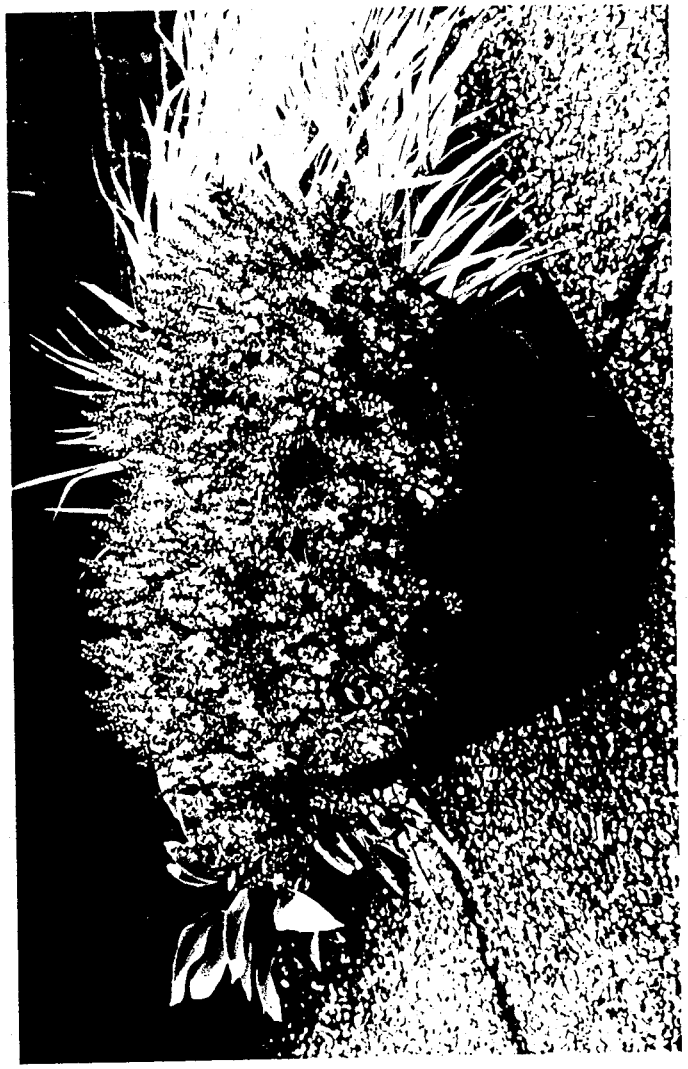
FIG. 3 is a view of the plant in a container emphasizing its compact habit.

The following is a detailed description of the new Hebe variety. All color determinations and comparisons are based on the Royal Horticultural Society Colour Chart.

Origin: Seedling selection.

Parentage: A cross between Hebe 'Carl Teschner' and Hebe 'Mauve Queen'.

Habit: Semi-dwarf to dwarf. Compact.

Size: Mature plants are about 160 mm (6 inches) tall with a spread of about 400 mm (16 inches).

Plant vigor: The shrub shows vigorous and healthy growth throughout Great Britain.

Blooming habit: Prolific. Entire shrub covered with a dense mass of blossom spikes.

Blooming period: Late May to early June with later flushes into late summer and fall.

Hardiness: Winter hardy throughout the British Isles. The plant has not been tested for maximum summer temperature tolerance.

FOLIAGE

Arrangement: Stiff, alternate and opposite on brownish, wiry stems.

Type: Evergreen leaves on woody shrub.

Texture: Glossy, very slightly hairy upper surface. Glossy, slightly hairy lower surface.

Shape: Elliptic.

Length: About 14 mm.

Width: About 6 mm.

Petiole: Absent.

Margins: Entire.

Apex: Cuspidate.

Base: Rounded.

FLOWERS

Petal:

*Count.*—Four.

*Shape.*—Elliptic.

Flower type: Joined at base in short tube. Zygomorphic.

Carpels: Very small.

Stamens: Very small.

Blooming habit: Approximately 30 flowers in axiallary racemes, some branched.

Blooming period: Late May or early June, followed by several flushes in later summer and fall.

COLOR CHARACTERISTICS

Foliage:

*Mature leaves.*—Upper surface RHS Fan 3, Green Group No. 143 B; lower surface RHS Fan 3, Green Group No. 143 C.

Flowers:

*Petals.*—RHS Fan 2, Violet-Blue Group No. 91 B, fading to Blue Group No. 108 C, then to white.

I claim:

1. A new and distinct cultivar of 'Hebe' substantially as shown and described, characterized by semi-dwarf to dwarf compact habit, profuse blooming in late May to early June with later flushes in late summer and fall, upstanding flower spikes appearing well above the foliage, the sky blue flowers fading to pale blue and then white giving a distinctive bicolor effect.

* * * * *